US009877646B2

(12) United States Patent
Stetson et al.

(10) Patent No.: US 9,877,646 B2
(45) Date of Patent: Jan. 30, 2018

(54) ASSESSMENT OF RETINAL DISRUPTION (71) Applicant: Carl Zeiss Meditec, Inc., Dublin, CA (US)

(72) Inventors: Paul F. Stetson, Piedmont, CA (US); Mary K. Durbin, San Francisco, CA (US)

(73) Assignee: Carl Zeiss Meditec, Inc., Dublin, CA (US)

( * ) Notice: Subject to any disclaimer, the term of this patent is extended or adjusted under 35 U.S.C. 154(b) by 105 days.

(21) Appl. No.: 13/648,556

(22) Filed: Oct. 10, 2012

(65) Prior Publication Data

US 2013/0286354 A1    Oct. 31, 2013

Related U.S. Application Data

(60) Provisional application No. 61/545,811, filed on Oct. 11, 2011.

(51) Int. Cl.
| | | |
|---|---|---|
| *A61B 3/10* | (2006.01) | |
| *G06T 7/00* | (2017.01) | |
| *G06T 7/12* | (2017.01) | |

(52) U.S. Cl.
CPC ........... *A61B 3/102* (2013.01); *G06T 7/0012* (2013.01); *G06T 7/12* (2017.01); *G06T 2207/10101* (2013.01); *G06T 2207/30041* (2013.01)

(58) Field of Classification Search
CPC .. A61B 3/10; A61B 3/103; A61B 3/14; A61B 3/152; A61B 3/04; A61B 3/113; A61B 3/1125; A61B 3/1225; A61B 3/107; A61B 3/1015; A61B 3/102; G06T 7/12; G06T 7/0012; G06T 2207/0101; G06T 2207/30041

USPC ....... 351/205, 206, 208, 210, 211, 212, 216, 351/221, 236, 246

See application file for complete search history.

(56) References Cited

U.S. PATENT DOCUMENTS

| | | |
|---|---|---|
| 7,347,548 B2 | 3/2008 | Huang et al. |
| 7,668,342 B2 | 2/2010 | Everett et al. |
| 7,997,728 B2 | 8/2011 | Huang et al. |

(Continued)

FOREIGN PATENT DOCUMENTS

WO    2010/080576 A1    7/2010

OTHER PUBLICATIONS

Christensen et al.,"Normative Data of Outer Photoreceptor Layer Thickness Obtained by Software Image Enhancing Based on Stratus Optical Coherence Tomography Images", Br. J. Ophthalmol, vol. 92, Nov. 28, 2012, pp. 800-805.

(Continued)

*Primary Examiner* — Jie Lei
(74) *Attorney, Agent, or Firm* — Morrison & Foerster LLP (57) ABSTRACT

Systems and methods for improving the assessment of disruption or abnormalities to retinal layers are presented. The disruptions are detected by analyzing at least one segmented boundary of optical coherence tomography data. Several different types of analysis can be used alone or in combination to make an assessment of the level of disruption to the particular boundary or layer defined by the boundary. The results can be presented as an end face image and quantified to report an amount of disruption. In one embodiment, a method for determining the disruption to the photoreceptor outer segment is described.

9 Claims, 4 Drawing Sheets

(56) References Cited

U.S. PATENT DOCUMENTS

| | | | |
|---|---|---|---|
| 8,045,176 B2 | 10/2011 | Everett et al. | |
| 8,223,143 B2 | 7/2012 | Dastmalchi et al. | |
| 8,332,016 B2 | 12/2012 | Stetson | |
| 2007/0216909 A1* | 9/2007 | Everett et al. | 356/479 |
| 2008/0100612 A1* | 5/2008 | Dastmalchi | G06F 19/321 345/418 |
| 2009/0268162 A1* | 10/2009 | Stetson | A61B 3/102 351/246 |
| 2012/0127427 A1 | 5/2012 | Guo et al. | |

OTHER PUBLICATIONS

Fischer et al., "A New Method to Monitor Visual Field Defects Caused by Photoreceptor Degeneration by Quantitative Optical Coherence Tomography", Investigative Ophthalmology & Visual Science, vol. 49, No. 8, Aug. 2008, pp. 3617-3621.

Haeker et al., "Use of Varying Constraints in Optimal 3-D Graph Search for Segmentation of Macular Optical Coherence Tomography Images", MICCAI, Part I, LNCS 4791, 2007, pp. 244-251.

Leitgeb et al., "Ultrahigh Resolution Fourier Domain Optical Coherence Tomography", Optics Express, vol. 12, No. 10, May 17, 2004, pp. 2156-2165.

Petzold Axel, "Microcystic Macular Oedema in MS: T2 Lesion or Black Hole?", The Lancet Neurology, vol. 11, No. 11, 2012, 2 pages.

Saidha et al., "Microcystic Macular Oedema, Thickness of the Inner Nuclear Layer of the Retina, and Disease Characteristics in Multiple Sclerosis: A Retrospective Study", The Lancet Neurology, vol. 11, No. 11, 2012, 10 pages.

Shahidi et al., "Quantitative Thickness Measurement of Retinal Layers Imaged by Optical Coherence Tomography", American Journal of Ophthalmology, vol. 139, No. 6, Jun. 2005, pp. 1056-1061.

Srinivasan et al., "Characterization of Outer Retinal Morphology with High-Speed, Ultrahigh-Resolution Optical Coherence Tomography", Investigative Ophthalmology & Visual Science, vol. 49, No. 4, Apr. 2008, pp. 1571-1579.

Szkulmowski et al., "Analysis of Posterior Retinal Layers in Spectral Optical Coherence Tomography Images of the Normal Retina and Retinal Pathologies", Journal of Biomedical Optics, vol. 12, No. 4, Jul./Aug. 2007, pp. 041207-1-041207-11.

Tan et al., "Detection of Macular Ganglion Cell Loss in Glaucoma by Fourier-Domain Optical Coherence Tomography", Ophthalmology, vol. 116, No. 12, Dec. 2009, pp. 2305-2314.

Villate et al., "Photoreceptor Layer Features in Eyes with Closed Macular Holes: Optical Coherence Tomography Findings and Correlation With Visual Outcomes", American Journal of Ophthalmology, vol. 139, No. 2, Feb. 2005, pp. 280-289.

Zawadzki et al., "Adaptation of a Support Vector Machine Algorithm for Segmentation and Visualization of Retinal Structures in Volumetric Optical Coherence Tomography Data Sets", Journal of Biomedical Optics, vol. 12, No. 4, Jul./Aug. 2007, pp. 041206-1-41206-8.

\* cited by examiner

ASSESSMENT OF RETINAL DISRUPTION

PRIORITY

This application claims priority to U.S. Provisional Application Ser. No. 61/545,811 filed Oct. 11, 2011 hereby incorporated by reference.

TECHNICAL FIELD

One or more embodiments of the present invention relate to analysis of optical coherence tomography data of the retina. In particular, it is an aspect of the present invention to improve the assessment of tissue integrity in areas where the thickness may deviate from normal by creating and analyzing a visual representation or map of detected disturbances to the normal anatomy of the retina.

BACKGROUND

The most common quantitative measurements made with optical coherence tomography (OCT) are thickness measurements. Examples include total retinal thickness in the macular area, retinal nerve fiber layer thickness (RNFL) in the peripapillary area, and other layer thicknesses such as ganglion cell complex thicknesses. For instance, the standard measurement used to assess edema or atrophy of the retina is a measurement of the thickness of the entire retina from the Internal Limiting Membrane (ILM) to the Retinal Pigment Epithelium (RPE). However, the visual acuity of a patient before or after treatment may bear little relation to thickness measurements. A more relevant assessment to some diseases, especially diseases known to affect the photoreceptor layer, may be made by analyzing images so as to assess the status of the photoreceptors, but thickness measurements may not be the most appropriate way of assessing the health of the photoreceptors. For example, the true thickness of a particular retinal layer may not vary smoothly with increasing pathology, but rather may exhibit more of a two-state behavior: either it appears healthy at a particular location or it does not, and the sign of the extent of pathology is the area of unhealthy tissue. Furthermore, the first signs of disease in a particular layer may be observed as disruptions that maintain most of the average thickness of the layer. These disruptions may be seen as alterations or variations in thickness, reflectivity, or other properties over an area of observation. An algorithm that attempts to give a consistent contour over disrupted areas may actually smooth out some local variations in tissue integrity and obscure signs of pathology.

SUMMARY

The present invention proposes to improve the assessment of tissue integrity in areas where the thickness may deviate from normal. This invention, in various embodiments, creates a visual representation or map of detected disturbances to the normal anatomy of the retina. The disruptions are detected by analyzing at least one segmented boundary or a layer or layers defined using that boundary. This can be accomplished by evaluating one or more parameters or characteristics across a range of transverse locations including but not limited to thickness, variability of thickness, brightness, variability of brightness, variability of the depth of a boundary and continuity of a boundary. The resulting map may be summarized by a reported area of abnormal tissue or a percentage of abnormal area in the total area of the retina that was scanned. In one embodiment, it is anticipated that this method would provide some ability to predict the visual acuity after resolution of edema by assessing the intactness of the photoreceptors in areas of pathology.

Photoreceptor Outer Segment (PROS) length, or thickness, can be measured by determining the distance between the segmentations of the RPE and the boundary between the Photoreceptor Inner and Outer Segments (IS/OS). Like Macular Thickness, the average PROS thickness within a specified area has been used to characterize both normal and diseased retinas. (see for example Shahidi et al, "Quantitative Thickness Measurement of Retinal Layers Imaged by Optical Coherence Tomography", American Journal of Ophthalmology, Vol. 139, No. 6. Jun. 2005, pp. 1056-1061, Christensen et al "Normative data of outer photoreceptor layer thickness obtained by software image enhancing based on Stratus optical coherence tomography images", British Journal of Ophthalmology, 92:800-805 2008, Villate et al "Photoreceptor layer features in eyes with closed macular holes: Optical coherence tomography findings and correlation with visual outcomes", American Journal of Ophthalmology, Vol. 139, Issue 2, Pages 280-289, and Srinivasan et al., "Characterization of Outer Retinal Morphology with High-Speed, Ultrahigh-Resolution Optical Coherence Tomography", IOVS v. 49, no. 4, Apr. 2008). In most pathologies, though, the PROS thickness is not continuously variable. Instead the IS/OS tends to be broadened, interrupted, or missing in focal regions, so PROS thickness at a particular point tends to be either near the normal range or near zero.

Since disruptive pathology can cause the IS/OS to disappear, one embodiment of the invention described herein measures the area of disrupted Photoreceptor Outer Segment by determining the area of Outer Segment length below a normal threshold (e.g., 18 microns, based on our observations of Outer Segment variation in normals). Thresholding the result can give an assessment that is more robust against small variations in segmentation length or uncertainty in the absence of clear boundaries for segmentation. This Abnormal Area could be reported as a percentage of the area being considered, e.g., percentage of overall scanned area or percentage of a particular subfield within that area. The area may alternatively be reported as an absolute number. The percentage of Abnormal Area is insensitive to normal variations in length. This metric more directly characterizes the amount of disruption in the IS/OS, as detected by an OCT segmentation algorithm.

In one study of retinitis pigmentosa patients, the distance from the fovea over which the IS/OS could be identified in 2-D Stratus scans was compared to extent of visual field (Dominik Fischer et al "A New Method to Monitor Visual Field Defects Caused by Photoreceptor Degeneration by Quantitative Optical Coherence Tomography", Invest. Ophthalmol. Vis. Sci. 49: 3617-3621 2008) This is similar to measurement of Abnormal Area in that it considers only whether the IS/OS has disappeared or not, but it is significantly different in that it is linear rather than areal, and in that it only defines a single distance from the fovea where the IS/OS (dis)appears, rather than making an assessment at each point.

In some of the embodiments of the present invention the disrupted tissue is detected using a single parameter indicating variability in a measurement. In one embodiment, the variance of the segmentation depth of a single boundary is estimated over a local region. A map of the variance conveys information about segmentation reliability, since it is related to the presence of an intact photoreceptor layer. It is a different assessment of photoreceptor disruption than the PROS thickness, one that quantifies the uncertainty of the segmentation in areas of atrophy and can be used as a metric of photoreceptor disruption. The assessment of photoreceptor disruption at each point in the map is a unitless index of photoreceptor disruption, predominantly relating to normative limits on Outer Segment thickness but also including a local estimate of the reliability of the segmentation.

Another embodiment of the invention is determining the abnormal area using multiple parameters. At each point in a 2-D retinal map, a set of parameters can be evaluated to assess whether that point is normal or pathological. The assessment may be different at different points in the retina, e.g., what is normal at the fovea may be abnormal elsewhere. This may be expressed mathematically as f(p(x,y);x,y), a scalar function of a vector field of parameters p(x,y) in which the function may also depend on the lateral coordinates (x,y). The multiple-parameter version of this invention has the advantage of summarizing a set of different measurements to give more tolerance to errors in any one of those individual measurements. It can also make use of the independent information the different measurements provide.

While the description is largely focused on the photoreceptor outer segment, this approach could also be applied to other retinal layer segmentations such as the Nerve Fiber Layer, External Limiting Membrane (ELM), Inner Nuclear Layer (INL) or Ganglion Cell Layer (GCL). The segmentations could be at the macula, the Optic Nerve Head, or elsewhere in the posterior pole.

The function may be a 'fuzzy' result, for example, an estimate of the likelihood of abnormality. Alternately, the result may be a 'crisp', thresholded result based on expected results or function values for sets of normal and diseased subjects. A fuzzy result may be the best presentation in cases where the overlap between normal and pathological results is substantial. In such cases, a moderate value may indicate a substantial possibility of either decision, and simply assigning an absolute decision would be less informative than a balanced answer.

DETAILED DESCRIPTION

The present invention provides methods for analyzing three dimensional image data collected of the eye using non-invasive imaging techniques such as optical coherence tomography (OCT). OCT is a noninvasive, noncontact imaging modality that uses coherence gating to obtain high-resolution cross-sectional images of tissue microstructure. In Fourier domain OCT (FD-OCT), the interferometric signal between light from a reference and the back-scattered light from a sample point is recorded in the frequency domain rather than the time domain. The spectral information discrimination in FD-OCT is accomplished either by using a dispersive spectrometer in the detection arm in the case of spectral-domain OCT (SD-OCT) or rapidly tuning a swept laser source in the case of swept-source OCT (SS-OCT).

Figure 1:
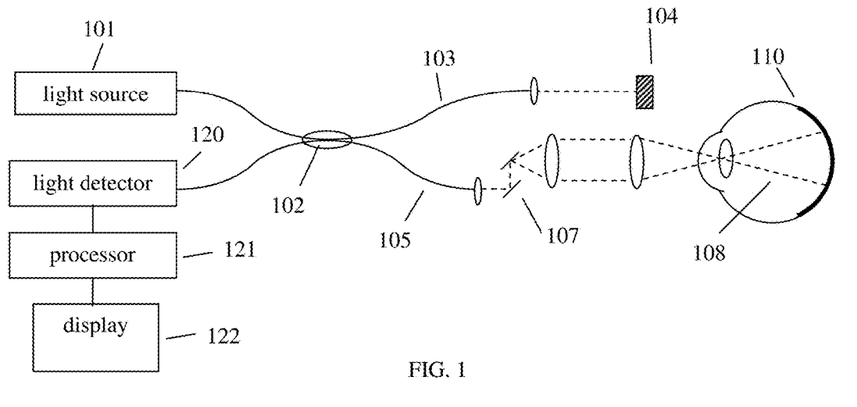
FIG. 1 illustrates the general components of an SD-OCT system used for collecting OCT imaging data of the eye.

A diagram of a generalized FD-OCT system is shown in FIG. 1. Light from source 101 is routed, typically by optical fiber 105, to illuminate the sample 110, a typical sample being tissues in the human eye. The source 101 can be either a broadband light source with short temporal coherence length in the case of SD-OCT or a wavelength tunable laser source in the case of SS-OCT. The light is scanned, typically with a scanner 107 between the output of the fiber and the sample, so that the beam of light (dashed line 108) is scanned laterally (in x and y) over the area or volume to be imaged. Light scattered from the sample is collected, typically into the same fiber 105 used to route the light for sample illumination. Reference light derived from the same source 101 travels a separate path, in this case involving fiber 103 and retro-reflector 104 with an adjustable optical delay. Those skilled in the art recognize that a transmissive reference path can also be used and that the adjustable delay could be placed in the sample or reference arm of the interferometer. Collected sample light is combined with reference light, typically in a fiber coupler 102, to form light interference in a detector 120. Although a single fiber port is shown going to the detector, those skilled in the art recognize that various designs of interferometers can be used for balanced or unbalanced detection of the interference signal. The output from the detector is supplied to a processor 121. The results can be stored in the processor 121 or displayed on display 122. The processing and storing functions may be localized within the OCT instrument or functions may be performed on an external processing unit to which the collected data is transferred. This unit could be dedicated to data processing or perform other tasks which are quite general and not dedicated to the OCT device.

The interference causes the intensity of the interfered light to vary across the spectrum. The Fourier transform of the interference light reveals the profile of scattering intensities at different path lengths, and therefore scattering as a function of depth (z-direction) in the sample (see for example Leitgeb et al. "Ultrahigh resolution Fourier domain optical coherence tomography," Optics Express 12(10):2156 (2004)). The profile of scattering as a function of depth is called an axial scan (A-scan). A set of A-scans measured at neighboring locations in the sample produces a cross-sectional image (tomogram or B-scan) of the sample. A collection of B-scans collected at different transverse locations on the sample makes up a data volume or cube.

The sample and reference arms in the interferometer could consist of bulk-optics, fiber-optics or hybrid bulk-optic systems and could have different architectures such as Michelson, Mach-Zehnder or common-path based designs as would be known by those skilled in the art. Light beam as used herein should be interpreted as any carefully directed light path. In time-domain systems, the reference arm needs to have a tunable optical delay to generate interference. Balanced detection systems are typically used in TD-OCT and SS-OCT systems, while spectrometers are used at the detection port for SD-OCT systems. The invention described herein could be applied to any type of OCT system capable of collecting data on the posterior section of the eye of a patient. The invention relates to processing of OCT data that can be done on the OCT instrument itself or on a separate computer or workstation to which collected OCT data is transferred either manually or over a networked connection.

In the present invention, the collected data is segmented to identify at least one retinal boundary for which further analysis is desired. The boundary could be one of a number of surfaces in the retina including but not limited to the inner segment/outer segment (IS/OS), the retinal pigment epithelium (RPE), the Nerve Fiber Layer (NFL), External Limiting Membrane (ELM), Inner Nuclear Layer (INL), inner limiting membrane (ILM), outer nuclear layer (ONL), the choroid or the Ganglion Cell Layer (GCL). The data segmentation can be automatic, semi-automatic, or manual. Various segmentation strategies are known to those skilled in the art. For instance, Tan et al describe using an iterative method based on gradients of reflectivity between layers (Tan et al., "Detection of Macular Ganglion Cell Loss in Glaucoma by Fourier-Domain Optical Coherence Tomography," Ophthalmology 2009; 116(12)). Such methods depend on signal detected independently in each A-scan. For three dimensional data, additional accuracy and repeatability can be obtained by including information from neighboring pixels, and by including information known about the expected layer architecture. Haeker et al., describe a graph-search method with varying constraints that allows the algorithm to be trained to expected layer smoothness constraints and expected separation distances between layers (Haeker et al., "Use of Varying Constraints in Optimal 3-D Graph Search for Segmentation of Macular optical Coherence Tomography Images," MICCAI 2007 Presentation 438). Another method that utilizes neighboring information is a Support Vector Machine based segmentation, described by Zawadzki et al. (Zawadzki et al., "Adaptation of a support vector machine algorithm for segmentation and visualization of retinal structures in volumetric optical coherence tomography data sets," J Biomed Opt. 2007; 12(4)). This method allows information about expected retinal structures to be input. Both of these methods require clinical input at some level—for the graph search method a training set is segmented by the user, while for the SVM method the user must select reference points located in specific layers on each image to be segmented. In the preferred embodiment of the present invention, OCT image data of the macula are segmented to yield the locations of the RPE and IS/OS boundaries as illustrated in the top panel of FIG. 3. These two boundaries define the photoreceptor outer segment layer.

Once segmented, a number of analyses can be made of the depths of the boundaries and the image data near or between those boundaries across a range of transverse values. Some examples of the types of analyses that can be performed include but are not limited to thickness, variability of thickness, brightness, variability of brightness, depth variation, and continuity of a boundary. The results of these separate analyses (parameters) can be used alone or combined to give an integrated assessment or index of the layer abnormality (in the case of the preferred embodiment photoreceptor integrity) over a range of transverse or lateral locations. Several different analyses will now be described in further detail.

Brightness of the OCT image data may be used as a means of characterizing disruption of a retinal layer. Image brightness may vary significantly due to variability among instruments or subjects, for example, the presence of cataracts or other tissues absorbing light before it reaches the retina. Because of this variability, the brightness in the layer of interest needs to be compared to brightness at some other point in the image, for example, a maximum brightness level for that A-scan, or the average brightness of the RPE. In another type of analysis, the difference in the depths of the layer boundaries can be determined directly from the segmentation and can then be compared to normative values to give information about the presence of photoreceptors.

An analysis can be made on the continuity of the boundary, in this case the IS/OS. One way to analyze the boundary continuity is to calculate the local variance in image brightness along the IS/OS contour. The brightness along the contour may be calculated by averaging the image intensity within a small vertical range around the segmentation depth at each lateral position.

$$X(j,k) = \frac{1}{N+M+1} \sum_{i_o=-M}^{N} x(i+i_o, j, k)$$

where N and M are the desired bounds of the averaging, for example, from 5 microns above to 5 microns below the segmentation, and x(i,j,k) is the 3-D image intensity. The local variance may be estimated by calculating the variance over a sliding window. This implies the calculation of the local mean using the same neighborhood, so that the deviation about this mean can be used to calculate variance:

$$M_X(j,k) = K(j,k) * X(j,k)$$
$$= \sum_{j_o=-W_j}^{W_j} \sum_{k_0=-W_k}^{W_k} K(j_0, k_0) X(j+j_0, k+k_0)$$

$$V_X(j,k) = K(j,k) * [X(j,k) - M_X(j,k)]^2$$
$$= \sum_{j_o=-W_j}^{W_j} \sum_{k_0=-W_k}^{W_k} K(j_0, k_0)$$
$$[X(j+j_0, k+k_0) - M_X(j+j_0, k+k_0)]^2$$

where $M_X$ and $V_X$ are the local mean and local variance of the image intensity along the segmentation contour, K is the averaging kernel, $W_j$ and $W_k$ are the half-widths of the averaging kernel, and X is the image intensity along the segmentation contour. In a preferred calculation of local variance, the kernel K contains a circle 200 microns in diameter inside a square (a square in physical dimensions, although not necessarily having an equal number of pixels in each lateral dimension if the pixels are not laterally isotropic). Using the definitions above requires the sum of the kernel elements to be 1 for averaging.

Similar analyses can be performed to determine the local variance in depth of the IS/OS and RPE segmentations and/or the local variance of the PROS thickness (the difference between these two segmentations):

$$M_Z(j,k) = K(j,k) * Z(j,k)$$
$$= \sum_{j_o=-W_j}^{W_j} \sum_{k_0=-W_k}^{W_k} K(j_0, k_0) Z(j+j_0, k+k_0)$$

$$V_Z(j,k) = K(j,k) * [Z(j,k) - M_Z(j,k)]^2$$
$$= \sum_{j_o=-W_j}^{W_j} \sum_{k_0=-W_k}^{W_k} K(j_0, k_0)$$
$$[Z(j+j_0, k+k_0) - M_Z(j+j_0, k+k_0)]^2$$

where $M_Z$ and $V_Z$ are the local mean and local variance of the segmentation depth or PROS thickness, K is the averaging kernel, $W_j$ and $W_k$ are the half-widths of the averaging kernel, and Z is the segmentation depth or PROS thickness. Other measures of variability include standard deviation, mean absolute deviation, or such others as may be devised by those skilled in the art.

Figure 2:
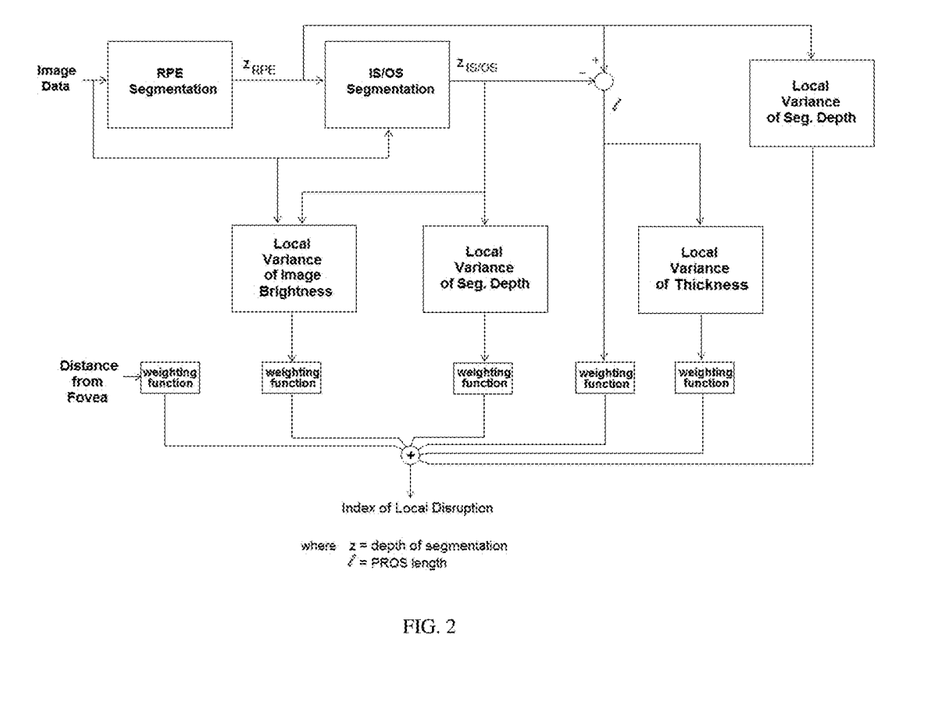
FIG. 2 illustrates one embodiment of the present invention.

FIG. 2 illustrates the steps of a generalized embodiment of the present invention using several of the analyses described above. First, image data is segmented to identify the RPE and IS/OS. This yields the depths of each boundary in the image data ($z_{RPE}$ and $z_{IS/OS}$). These two segmentations are then analyzed to determine a variety of parameters including the PROS length or thickness (l), the local variance of each segmentation depth, the local variance of the PROS thickness, and the local variance of the image brightness at the depth of the IS/OS segmentation. The results from these analyses can be compared to expected values by a weighting function that gives a result near or equal to zero when the input values are within expected ranges and outputs a higher value when the input values are outside the expected ranges; the highest values output by the function are determined by the weight that the analysis of that parameter has on the overall decision. In the preferred embodiment, for example, the maximum output of the weighting function that evaluates the local mean of the PROS length is twice the maximum output of the weighting function that evaluates the local variance of the PROS length. The expected values could most easily be determined from a point by point evaluation of a collection of normative data. The location of the fovea in the scan is also used as context for interpreting the other input parameters, with a small distance compensating for the increased local variance in IS/OS depth that is normally observed there. The end result is an index of local disruption that can be displayed in an en face presentation or image. The index can also be used to calculate the amount or area of abnormal tissue and this could be further reported as a percentage of abnormal tissue over a specific region or scan area. While this embodiment compares the parameters to expected values prior to combining into an index, an index can also be imagined based purely on a combination of the parameters without the comparison.

Figure 3:
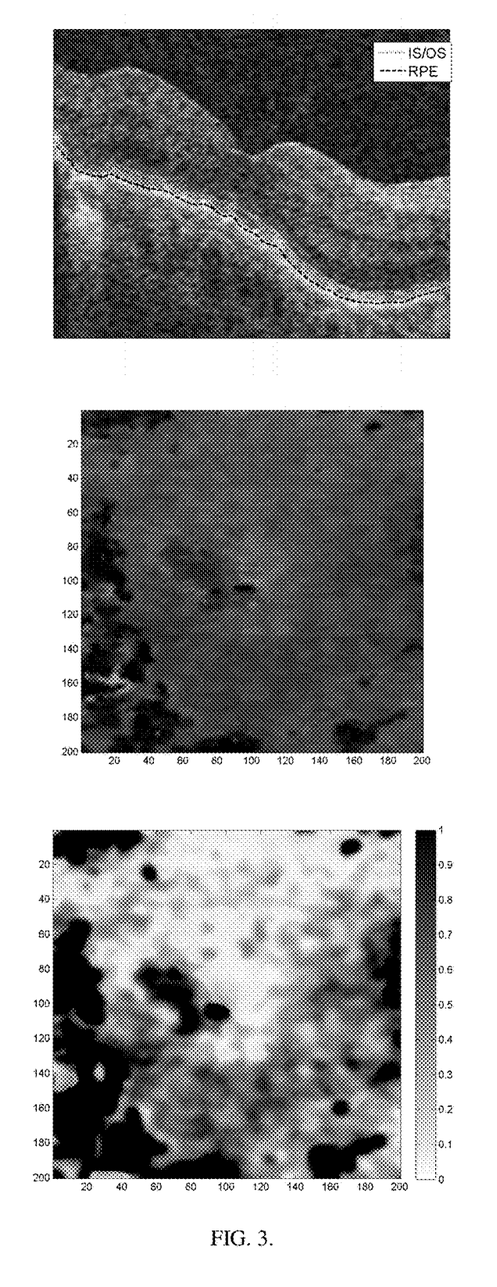
FIG. 3 shows an example of PROS segmentation (top), PROS thickness map (middle) and map of photoreceptor disruption incorporating thickness and local variance information (bottom).
Figure 4:
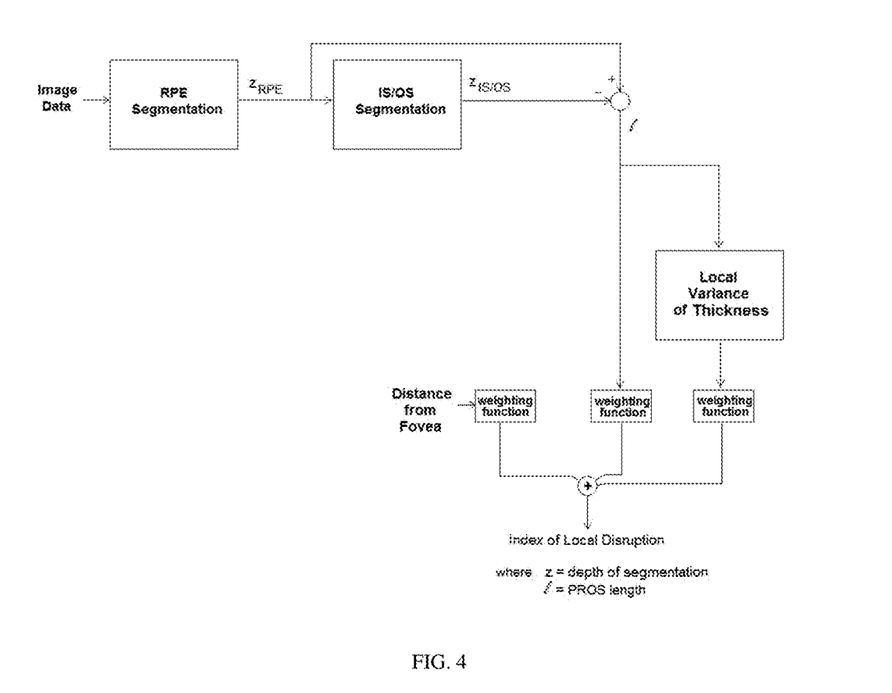
FIG. 4 illustrates the steps involved with another embodiment of the present invention.

In the steps of the preferred embodiment of the invention shown in FIG. 4, the image data from an OCT instrument scan of the macula are segmented to yield the locations of the RPE and IS/OS boundaries similar to the embodiment illustrated in FIG. 2. However in this embodiment, only two parameters of the segmented data are calculated. The difference in the depths ($z_{RPE}$ and $z_{IS/OS}$) of the segmentations gives a measurement of the PROS layer thickness (l), which is then compared to normative values to give an input to the index of local disruption. The local variance of the thickness is compared to normal values to give another input. These two analyses of the PROS thickness, together with a weighting factor based on distance to the fovea, are combined to give the index of local disruption that gives an assessment of the integrity of the photoreceptors at that location in the map. FIG. 3 shows the results of the analysis in this embodiment over a 6 mm by 6 mm tissue region (representing 512 by 128 pixels). The top panel shows the PROS layer segmentations, the middle panel shows the thickness map of the PROS generated by taking the difference between the two segmentation depths, and the bottom panel shows a map or en face image of the photoreceptor disruption index incorporating thickness and local variance of thickness as described in FIG. 4. This index may be compared to a threshold to give a crisp decision about the location of abnormal regions of the photoreceptors.

Figure 5:
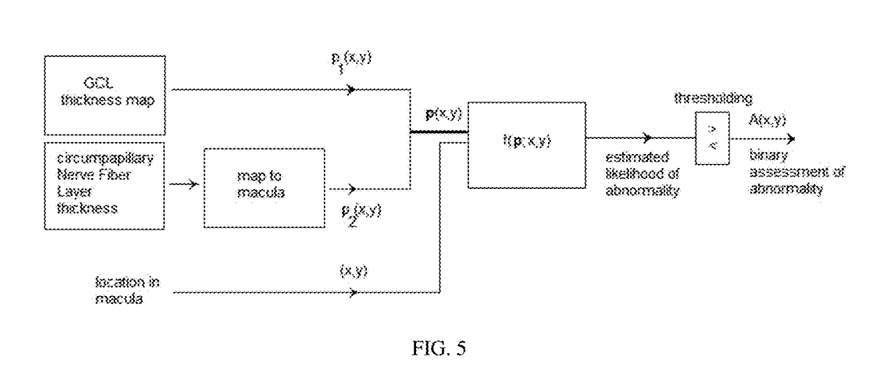
FIG. 5 illustrates the steps involved with still another embodiment of the present invention.

Another, more general embodiment of the present invention is illustrated in FIG. 5. Here thicknesses of the Ganglion Cell Layer (GCL) and the Nerve Fiber Layer (NFL) have been determined based on segmentations of the boundaries of these layers. The peripapillary NFL map can be transformed to correspond to the points in the macula where the nerve fibers lead. In FIG. 5, the parameters to be included in the disruption map include the thickness of the ganglion cell layer, the thickness of the retinal nerve fiber layer, and a map of local correlations between each macular location and the set of peripapillary locations determined by the NFL map. The location in the macula is also used as context for interpreting the other input parameters. At each transverse location, the data from the GCL and NFL macula maps are analyzed in the context of their location in the macula and a statistical estimated likelihood of abnormality can be generated equivalent to the index of local disruption described in reference to FIGS. 2 and 4. The transverse location of the parameters can be expressed mathematically as f(p(x,y);x,y), a scalar function of a vector field of parameters p(x,y) in which the function may also depend on the lateral coordinates (x,y). Once the location dependence is accounted for, an estimated likelihood of normality can be made by comparing to expected values and an overall binary assessment of abnormality can be achieved. This arrangement looks beyond the photoreceptor layer in determining disruption of the retina.

In an alternative embodiment of the invention, a map of the variability of brightness within the inner nuclear layer might help identify maculas with edema in this layer, which has been associated with certain subjects with multiple sclerosis (see for example Saidha et al. "Microcystic macular oedema, thickness of the inner nuclear layer of the retina, and disease characteristics in multiple sclerosis: a retrospective study" The Lancet Neurology 10.1016/S1474-4422(12) 70213-2 and Petzold et al. "Microcystic macular oedema in MS: T2 lesion or black hole" The Lancet Neurology 10.1016/S1474-4422(12)70231-4). The eyes of these subjects show thickening of the inner nuclear layer as well as characteristic cysts. Volume searches for such cysts are laborious, which would make routine detection difficult. Furthermore, because the inner nuclear layer is a very thin layer, edema might not be noticed via deviation of the thickness of the total macula from normal. A disruption map showing variability of intensity (cysts have low brightness while the surrounding tissue is brighter) may be an excellent method of indicating the presence of this abnormality.

A benefit of presenting parameters as a map of disruption (that is, disruption as a function of transverse location) is that such disruptions can then be visualized in a way that makes clear the relationship to anatomical or pathological features of interest, such as blood vessels, neovascular membranes, the optic disc or the fovea. The OCT data itself can contain anatomical information, such as the location of blood vessels, the optic disc, the location of membranes or cysts, and the fovea, or the OCT data can be aligned in an en face manner to, for instance, a fundus image with detailed anatomical information. The disruption information can then be presented overlaid on the anatomical information.

Although various embodiments that incorporate the teachings of the present invention have been shown and described in detail herein, those skilled in the art can readily devise other varied embodiments that still incorporate these teachings. In particular the concept of identifying abnormal tissue could be extended to other layers of interest and imaging modalities.

The following references are hereby incorporated by reference:

PATENT DOCUMENTS

U.S. Pat. No. 7,668,342 Everett et al. "Method of bioimage data processing for revealing more meaningful anatomic features of diseased tissue"
U.S. Pat. No. 8,045,176 Everett et al. "Methods for mapping tissue with optical coherence tomography data."
U.S. Pat. No. 8,223,143 Dastmalchi et al. "User interface for efficiently displaying relevant OCT imaging data"
US Patent Publication No. 2012/0127427 Guo et al. "3D Retinal disruptions detection using optical coherence tomography"
U.S. Pat. No. 7,997,728 Huang et al. "Mapping and diagnosis of macular edema by optical coherence tomography"
PCT Publication No. WO 2010/080576 Debuc et al. "System and method for early detection of diabetic retinopathy using optical coherence tomography"
U.S. Pat. No. 7,347,548 Huang et al. "Method and apparatus for measuring a retinal sublayer characteristic"

NON-PATENT LITERATURE

Shahidi et al. "Quantitative Thickness Measurement of Retinal Layers Imaged by Optical Coherence Tomography", American Journal of Ophthalmology, Vol. 139, No. 6. (Jun. 2005), pp. 1056-1061.
Christensen et al. "Normative data of outer photoreceptor layer thickness obtained by software image enhancing based on Stratus optical coherence tomography images", British Journal of Ophthalmology, 92:800-805 (2008).
Villate et al. "Photoreceptor layer features in eyes with closed macular holes: Optical coherence tomography findings and correlation with visual outcomes", American Journal of Ophthalmology, Vol. 139, Issue 2, Pages 280-289.
Srinivasan et al., "Characterization of Outer Retinal Morphology with High-Speed, Ultrahigh-Resolution Optical Coherence Tomography", IOVS v. 49, no. 4, Apr. 2008.
Dominik Fischer et al. "A New Method to Monitor Visual Field Defects Caused by Photoreceptor Degeneration by Quantitative Optical Coherence Tomography", Invest. Ophthalmol. Vis. Sci. 49: 3617-3621 (2008).
Haeker et al., "Use of Varying Constraints in Optimal 3-D Graph Search for Segmentation of Macular optical Coherence Tomography Images," MICCAI 2007 Presentation 438.
Leitgeb et al. "Ultrahigh resolution Fourier domain optical coherence tomography," Optics Express 12(10):2156 (2004).
Tan et al., "Detection of Macular Ganglion Cell Loss in Glaucoma by Fourier-Domain Optical Coherence Tomography," Ophthalmology 2009; 116(12).
Saidha et al. "Microcystic macular oedema, thickness of the inner nuclear layer of the retina, and disease characteristics in multiple sclerosis: a retrospective study" The Lancet Neurology 10.1016/S1474-4422(12)70213-2.
Zawadzki et al., "Adaptation of a support vector machine algorithm for segmentation and visualization of retinal structures in volumetric optical coherence tomography data sets," J Biomed Opt. 2007; 12(4).
Szkulmowski at al. "Analysis of posterior retinal layers in spectral optical coherence tomography images of the normal retina and retinal pathologies" Journal of Biomedical Optics 12(4), 0141207-1-0141207-11.
Petzold et al. "Microcystic macular oedema in MS: T2 lesion or black hole" The Lancet Neurology 10.1016/S1474-4422(12)70231-4.

What is claimed is:

1. A method of analyzing 3D optical coherence tomography imaging data of an eye of a patient, said method comprising:
   collecting OCT image data over a plurality of transverse locations of the retina of a patient;
   segmenting the 3D data to identify boundaries associated with the retinal pigment epithelium (RPE), the photoreceptor inner segment (IS) and the photoreceptor outer segment (OS);
   calculating the photoreceptor outer segment thickness and the variability of the thickness of the photoreceptor outer segment based on the differences in the depths of the RPE and the IS/OS boundary;
   generating an index value at each of a plurality of transverse locations said index values corresponding to an integrated assessment of disruption, said index values being generated by combining the calculated photoreceptor outer segment thickness and the variability of thickness of the photoreceptor outer segment at each of the plurality of transverse locations using a factor associated with each selected parameter, said factor being based on the weight that the analysis of that parameter has on the overall determination of disruption;
   generating an en face image based upon the generated index values; and
   displaying the en face image.

2. The method as recited in claim 1, further comprising comparing the calculated parameters to expected values at a plurality of transverse locations and displaying an en face image of the comparison, said expected values being determined based on a collection of normative data.

3. The method as recited in claim 2, further comprising quantifying the amount of disruption and displaying the amount.

4. The method as recited in claim 1, further comprising weighting the parameters based on the transverse location within the retina.

5. The method as recited in claim 4, further comprising determining the percentage of disruption and displaying the percentage.

6. The method as recited in claim 1, where the en face image of disruption is presented in a manner that is aligned to an image that contains anatomical information, such as a fundus image that shows blood vessels and the optic disc.

7. A method of analyzing 3D optical coherence tomography imaging data of an eye of a patient, said method comprising:
   collecting OCT image data over a plurality of transverse locations of the retina of a patient;
   segmenting the 3D data to identify the boundaries associated with the Ganglion Cell Layer (GCL) and the Nerve Fiber Layer (NFL);
   calculating the thicknesses of the GCL and the NFL;
   generating an index value at each of a plurality of transverse locations, said index values corresponding to a statistically estimated likelihood of abnormality, said index values being generated by combining the calculated GCL and NFL thicknesses in view of a map of local correlations between each macular location and a set of peripapillary locations;

generating an en face image based upon the generated index values; and displaying the en-face image.

8. The method as recited in claim 7, further comprising comparing the index values to expected values, said expected values being determined based on a collection of normative data.

9. The method as recited in claim 7, where the en face image is presented in a manner that is aligned to an image that contains anatomical information, such as a fundus image that shows blood vessels, neovascular membranes, the optic disc or the fovea.

* * * * *

UNITED STATES PATENT AND TRADEMARK OFFICE
CERTIFICATE OF CORRECTION

PATENT NO.         : 9,877,646 B2
APPLICATION NO.    : 13/648556
DATED              : January 30, 2018
INVENTOR(S)        : Paul F. Stetson et al.

It is certified that error appears in the above-identified patent and that said Letters Patent is hereby corrected as shown below:

On the Title Page

In item (57), in Column 2, in "Abstract", Line 8, delete "end" and insert -- en --, therefor.

In the Specification

In Column 9, Line 11, delete "tissue"" and insert -- tissue." --, therefor.

In Column 9, Line 15, delete "data"" and insert -- data." --, therefor.

In Column 9, Line 18, delete "tomography"" and insert -- tomography." --, therefor.

In Column 9, Lines 20-21, delete "tomography"" and insert -- tomography." --, therefor.

In Column 9, Line 24, delete "tomography"" and insert -- tomography." --, therefor.

In Column 9, Line 26, delete "characteristic"" and insert -- characteristic." --, therefor.

In the Claims

In Column 11, Line 5, in Claim 7, delete "en-face" and insert -- en face --, therefor.

Signed and Sealed this
Nineteenth Day of June, 2018

Andrei Iancu
*Director of the United States Patent and Trademark Office*